(12) United States Patent
Chaung et al.

(10) Patent No.: US 7,749,979 B2
(45) Date of Patent: Jul. 6, 2010

(54) CPG DNA ADJUVANT IN AVIAN VACCINES

(75) Inventors: Hso-Chi Chaung, Pingtung County (TW); Li-Hsiang Hung, Kaohsiung (TW); Yi-Yang Lien, Pingtung County (TW)

(73) Assignee: National Pingtung University of Science and Technology, Pingtung County (TW)

( * ) Notice: Subject to any disclaimer, the term of this patent is extended or adjusted under 35 U.S.C. 154(b) by 0 days.

(21) Appl. No.: 12/260,122

(22) Filed: Oct. 29, 2008

(65) Prior Publication Data

US 2010/0003288 A1 Jan. 7, 2010

(30) Foreign Application Priority Data

Jul. 4, 2008 (TW) .............................. 97125312 A

(51) Int. Cl.
  A61K 31/70 (2006.01)
  A61K 39/38 (2006.01)
  A61K 39/295 (2006.01)
  A61K 39/17 (2006.01)
  A01N 43/04 (2006.01)

(52) U.S. Cl. ................ 514/44 R; 424/184.1; 424/201.1; 424/214.1; 424/826; 424/816

(58) Field of Classification Search ........................ None
See application file for complete search history.

(56) References Cited

U.S. PATENT DOCUMENTS

| | | | |
|---|---|---|---|
| 6,194,388 B1 * | 2/2001 | Krieg et al. ................ | 514/44 A |
| 6,207,646 B1 * | 3/2001 | Krieg et al. ................ | 514/44 R |
| 6,218,371 B1 * | 4/2001 | Krieg et al. ................ | 514/44 R |
| 6,406,705 B1 * | 6/2002 | Davis et al. .............. | 424/278.1 |
| 6,589,940 B1 * | 7/2003 | Raz et al. .................... | 514/44 R |
| 6,821,957 B2 * | 11/2004 | Krieg et al. ................ | 514/44 R |
| 6,949,520 B1 * | 9/2005 | Hartmann et al. ......... | 514/44 R |
| 6,977,245 B2 * | 12/2005 | Klinman et al. ............ | 514/44 R |
| 7,223,741 B2 * | 5/2007 | Krieg ....................... | 514/44 R |
| 7,271,156 B2 * | 9/2007 | Krieg et al. ................ | 514/44 A |
| 7,488,490 B2 * | 2/2009 | Davis et al. .............. | 424/278.1 |
| 7,514,415 B2 * | 4/2009 | Klinman et al. ............ | 514/44 R |
| 7,534,772 B2 * | 5/2009 | Weiner et al. ............. | 514/44 R |
| 7,569,553 B2 * | 8/2009 | Krieg ....................... | 514/44 R |
| 7,576,066 B2 * | 8/2009 | Krieg ....................... | 514/44 R |
| 2002/0164341 A1 * | 11/2002 | Davis et al. .............. | 424/184.1 |
| 2003/0091599 A1 * | 5/2003 | Davis et al. .............. | 424/278.1 |
| 2003/0181406 A1 * | 9/2003 | Schetter et al. ................ | 514/44 |
| 2003/0212026 A1 * | 11/2003 | Krieg et al. .................... | 514/44 |
| 2003/0224010 A1 * | 12/2003 | Davis et al. .............. | 424/185.1 |
| 2004/0053880 A1 * | 3/2004 | Krieg ............................ | 514/44 |
| 2004/0067905 A1 * | 4/2004 | Krieg ............................ | 514/44 |
| 2004/0092472 A1 * | 5/2004 | Krieg ............................ | 514/44 |
| 2004/0131628 A1 * | 7/2004 | Bratzler et al. ........... | 424/184.1 |
| 2004/0152649 A1 * | 8/2004 | Krieg ............................ | 514/44 |
| 2004/0186067 A1 * | 9/2004 | Krieg et al. .................... | 514/44 |
| 2004/0198680 A1 * | 10/2004 | Krieg ............................ | 514/44 |
| 2004/0235770 A1 * | 11/2004 | Davis et al. .................... | 514/44 |
| 2004/0266719 A1 * | 12/2004 | McCluskie et al. ............ | 514/44 |
| 2005/0032734 A1 * | 2/2005 | Krieg et al. .................... | 514/44 |
| 2005/0123550 A1 * | 6/2005 | Laurent et al. ........... | 424/184.1 |
| 2005/0130918 A1 * | 6/2005 | Agrawal et al. ................ | 514/44 |
| 2005/0197314 A1 * | 9/2005 | Krieg et al. .................... | 514/44 |
| 2005/0238660 A1 * | 10/2005 | Babiuk et al. ............ | 424/204.1 |
| 2006/0094683 A1 * | 5/2006 | Krieg et al. .................... | 514/44 |
| 2006/0287263 A1 * | 12/2006 | Davis et al. .................... | 514/44 |
| 2007/0066554 A1 * | 3/2007 | Krieg et al. .................... | 514/44 |
| 2007/0087986 A1 * | 4/2007 | Premack et al. ................ | 514/44 |
| 2007/0184465 A1 * | 8/2007 | Wagner et al. .................. | 435/6 |
| 2007/0212328 A1 * | 9/2007 | Bruck et al. ............... | 424/85.2 |
| 2007/0212329 A1 * | 9/2007 | Bruck et al. ............... | 424/85.2 |
| 2008/0226649 A1 * | 9/2008 | Schetter et al. .......... | 424/141.1 |
| 2009/0017021 A1 * | 1/2009 | Davis et al. .............. | 424/133.1 |
| 2009/0081157 A1 * | 3/2009 | Kornbluth et al. .......... | 424/85.2 |
| 2009/0081725 A1 * | 3/2009 | Powell et al. .............. | 435/69.1 |
| 2009/0155307 A1 * | 6/2009 | Davis et al. .............. | 424/204.1 |
| 2009/0169636 A1 * | 7/2009 | O'Hagan et al. ............ | 424/499 |
| 2009/0191188 A1 * | 7/2009 | Krieg et al. .............. | 424/130.1 |
| 2009/0324641 A1 * | 12/2009 | Dominowski et al. .... | 424/207.1 |
| 2010/0003288 A1 * | 1/2010 | Chaung et al. ........... | 424/278.1 |

OTHER PUBLICATIONS

Li et al, Xumu Shouyi Xuebao, 2006, 37/1:44-49 abstract only.*
Christopher et al, recent Developments on the Avian Influenza (H5N1) Crisis, 2006, pp. 85-118 abstract only.*
Chaung, International Immunopharmacology, 2006, 6:1586-1596.*
Pavlova et al, Vaccine, 2009, 27:773-785.*
Chen et al, J. Virology, Sep. 2001, 75/17:7956-7965.*
Dalloul et al, Expert Rev. Vaccines, 2006, 5/1:143-163.*
Dalloul et al, Avian Diseases, Dec. 2004, 48/4:783-790 abstract only.*
Dalloul et al, FASEB Journal, 2004, 18/4-5,Abstract 327.10 abstract only.*
Babiuk et al, Poultry Science, 2003, 82:870-875.*
Haygreen et al, Expert Rev. Vaccines, 2005, 4/1:51-62.*
Vleugels et al, Poultry Science, 2002, 81:1317-1321.*
Dalloul et al, Vaccine, 2005, 23:3108-3113.*
He et al, FEMS Immunology and Medical Microbiology, 2005, 43:81-89.*
Linghua et al, Veterinary Immunology and Immunopathology, 2007, 115:216-222.*
Wang et al, Avian Diseases, 2003, 47:1305-1312.*
Gomis et al, Infection and Immunity, Feb. 2003, 71/2:857-863.*
Mutwiri et al, Veterinary Immunology and Immunopathology, 2003, 91:89-103.*

* cited by examiner

Primary Examiner—N. M Minnifield
(74) Attorney, Agent, or Firm—Thomas, Kayden, Horstemeyer & Risley

(57) ABSTRACT

A CpG DNA adjuvant in avian vaccines is disclosed, which includes an immunostimulatory oligodeoxynucleotide (ODN) having a sequence of SEQ ID NO: 2. The CpG DNA adjuvant in avian vaccines is advantageous to carry out large-scale production, specifically enhance avian innate and adaptive immune responses, and the CpG DNA adjuvant is hardly to be digested by DNase due to its particular structures.

3 Claims, 4 Drawing Sheets

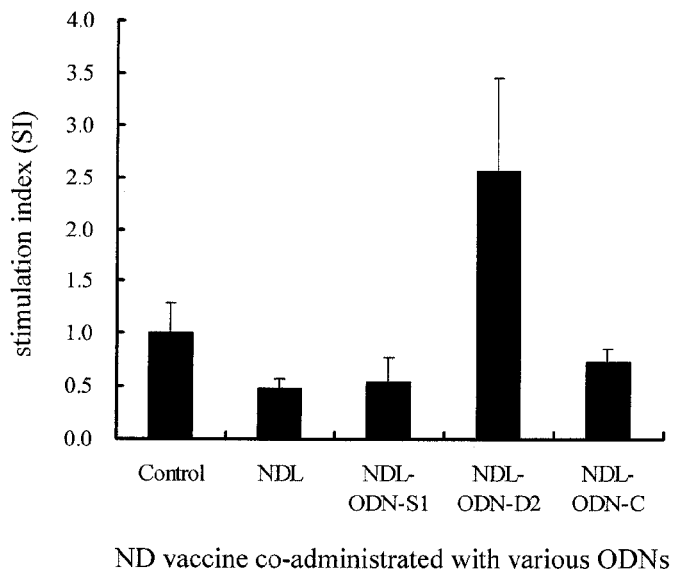
Fig. 5A
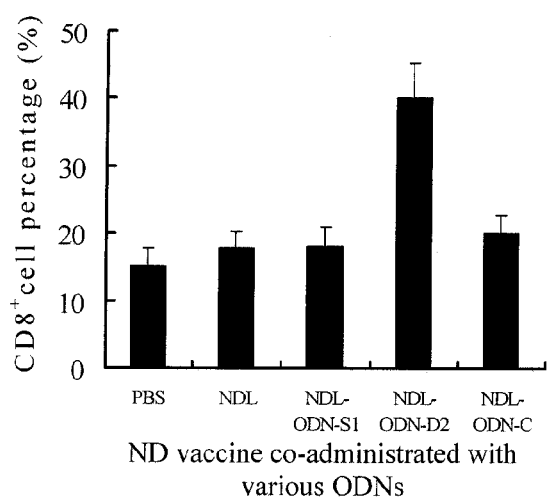 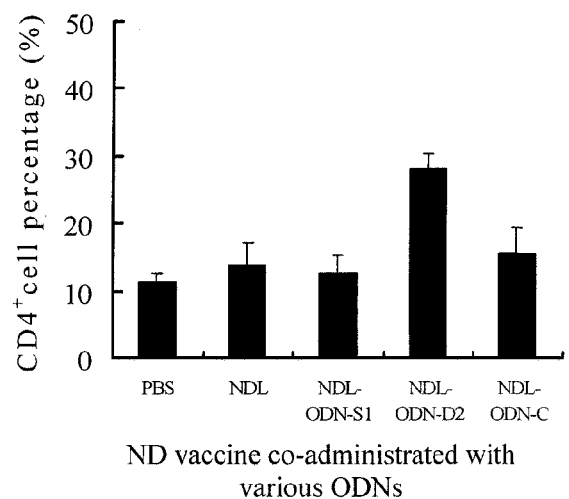
Fig. 5B
Fig. 5C

US 7,749,979 B2

CPG DNA ADJUVANT IN AVIAN VACCINES

RELATED APPLICATIONS

This application claims priority to Taiwan Application Serial Number 97125312, filed Jul. 4, 2008, which is herein incorporated by reference.

FIELD OF THE INVENTION

This invention relates generally to a vaccine adjuvant, and more particularly, to a CpG DNA adjuvant in avian vaccines.

BACKGROUND OF THE INVENTION

Adjuvant is a key component in vaccine development. In current avian vaccines, there are some disadvantages existing in the conventional adjuvant such as aluminum hydroxide gel adjuvant and oil adjuvant. For example, the above two adjuvants are chemical adjuvants that cannot enhance specific Th1 cell immune response. Especially, the conventional adjuvant cannot stimulate enough innate and adaptive immune responses against infections.

Therefore, Krieg A. M. et al. found that unmethylated dinucleotide CpG motifs in bacterial deoxyribonucleic acid (DNA) has advantages on stimulating several immune cells to secrete cytokines for enhancements of innate and adaptive immunity. See Krieg A. M. et al., Nature 374:546-549, 1995. The effectiveness of the DNA containing CpG motifs has been confirmed in 1998. The DNA containing CpG motifs has been used as a vaccine adjuvant in 2003. Moreover, the oligodeoxynucleotides (ODN) containing CpG motif can enhance the activities of lymphocytes and antigen-presenting cells (APC), trigger dendritic cell (DC) maturation and antigen-presenting function, and drive immune systems toward Th1 cell immune response against specific antigens, in several large domestic animals such as cattle, pigs, sheep etc. For example, one of the present inventors has provided an ODN containing porcine-specific phosphorothioate (PTO)-modified CpG motif, as well as an immunostimulatory plasmid containing various sets of CpG motifs specifically to pigs.

In general, the mechanisms involved in enhancing immune responses by the ODNs containing CpG motifs (CpG ODN) can be as follows. At first, CpG ODN enhances DC activation, maturation and antigen-presenting function. Secondly, CpG ODN increases DC migration. Thirdly, CpG ODN significantly elevates expression of DC cell markers such as MHC-II, CD40, CD80, CD86, and IL-12 in mice and human. Fourthly, CpG ODN induces priming DC more responsive to antigen-specific Th1 cells. Fifthly, CpG ODN increases CD8$^\square$ T cell cytotoxicity activity (CTL) to specific viruses or tumor cells. With application of CpG ODN, CpG ODN itself induces innate immune response to confer protective immune response against infection by viruses, bacteria and extracellular parasites, and B cells are activated by CpG ODN and vaccines to produce antibodies, to activate APC for secreting cytokines such as interferon-γ (IFN-γ), so as to enhance the immune response to vaccines.

However, the prior ODN containing PTO-modified CpG motif DNA synthesized by chemical processes is time-consuming, costs expensively and cannot be produced in mass. The CpG ODN is suitable for an adjuvant instead of PTO-modified CpG ODN. Typically, the CpG ODN contains unmethylated CpG motif, but without replacement of a phosphor atom of a phosphodiester bond in the PTO-modified CpG ODN with a sulfur atom, by which the phosphothioate reduces the degradation rate of the PTO-modified CpG ODN digested by deoxyribonuclease (DNase). In addition, the sequence of CpG ODN is species-specific; the CpG structures between different species are different in immunostimulatory activity. Currently, the sequence of most effective immuno-regulatory CpG motif is different between human and mice, and thus specific CpG motifs effective in various species are necessarily confirmed by experiments. The CpG ODN was applied to enhance poultry immunity since 2002. Related researches on the effectiveness of CpG ODN in poultry are mostly involved in evaluation of chemically synthesized CpG ODN in vitro, or focused on antibodies-related humoral immune response in vivo; investigation on the adjuvanicity of CpG ODN on the cell-mediated immune response effectively against viral infection in avians is very limited.

Hence, it is necessary to provide an effective avian immunostimulatory CpG ODN as the DNA adjuvant in avian vaccines, thereby overcoming the disadvantages of the prior DNA adjuvant modified by chemical processes complicatedly.

SUMMARY OF THE INVENTION

Accordingly, an aspect of the present invention provides a CpG DNA adjuvant in avian vaccines, which includes an immunostimulatory oligodeoxynucleotide (ODN) having a plurality of TCG tandem repeats at a 5' end, a poly-G structure at a 3' end, and at least one CpG motif with avian specific flanking sequences at two ends thereof between the 5' end and the 3' end. The CpG DNA adjuvant in avian vaccines is advantageous to carry out large-scale production, specifically to enhance avian innate and adaptive immune responses, and to facilitate cellular uptake of the CpG DNA adjuvant.

According to the aforementioned aspect of the present invention, a CpG DNA adjuvant in avian vaccines is provided, which includes an immunostimulatory ODN having a plurality of TCG tandem repeats at a 5' end, a poly-G structure essentially consisted of 4 to 6 guanines at a 3' end, and at least one unmethylated CpG motif with avian specific flanking sequences at two ends thereof between the 5' end and the 3' end thereof.

In a preferred embodiment, the immunostimulatory ODN may include but be not limited in a first ODN (CTAGTGTCCA TGACGTTATG GGGGGGT, denoted as SEQ ID NO:1), a second ODN (CTAGTTCGTC GAAGTCGTTT TGGGGGGT, denoted as SEQ ID NO:2), a third ODN (CTAGTTCGAT CATCGTTGAG GGGGGT, denoted as SEQ ID NO:3) or any combination thereof.

In a preferred embodiment, the immunostimulatory ODN may further include a first restriction enzyme site at the 5' end.

In a preferred embodiment, the immunostimulatory ODN may further include a second restriction enzyme site in a different sequence from the first restriction enzyme site at the 3' end.

In a preferred embodiment, the avian vaccines may be, for example, Newcastle Disease (ND) live vaccine, ND inactivated vaccine, avian influenza inactivated vaccine, or fowl cholera inactivated bacterin.

With application to the aforementioned CpG DNA adjuvant in avian vaccines of the present invention, it includes an immunostimulatory oligodeoxynucleotide (ODN) having a plurality of TCG tandem repeats at a 5' end, a poly-G structure at a 3' end, and at least one CpG motif with avian specific flanking sequences at two ends thereof between the 5' end and the 3' end. The CpG DNA adjuvant in avian vaccines is advantageous to carry out large-scale production, specifically to enhance avian innate and adaptive immune responses, and to facilitate cellular uptake of the CpG DNA adjuvant, instead of the prior DNA adjuvant modified by chemical processes complicatedly.

BRIEF DESCRIPTION OF THE DRAWINGS

The foregoing aspects and many of the attendant advantages of this invention are more readily appreciated as the same become better understood by reference to the following detailed description, when taken in conjunction with the accompanying drawing, wherein:

FIG. 5A is a bar chart of stimulation index (SI) of splenocytes of chickens co-immunized with the ND vaccine and various CpG DNA adjuvant according to a preferred embodiment of the present invention.

FIG. 5B is a bar chart of CD8 cell percentage of chickens co-immunized with the ND vaccine and various CpG DNA adjuvant according to a preferred embodiment of the present invention.

FIG. 5C is a bar chart of CD4 cell percentage of chickens co-immunized with the ND vaccine and various CpG DNA adjuvant according to a preferred embodiment of the present invention.

DETAILED DESCRIPTION OF THE PREFERRED EMBODIMENT

Figures 1A, 1B:
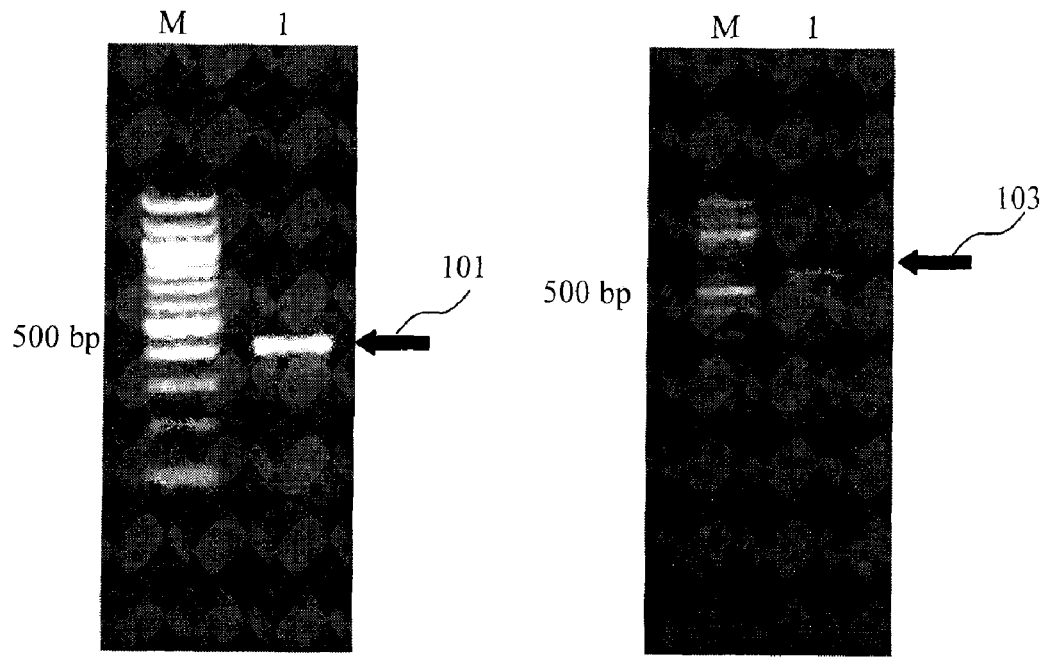
FIG. 1A is an electrophoresis image of PCR product for analyzing the avian β-actin gene according a preferred embodiment of the present invention.
FIG. 1B is an electrophoresis image of PCR product for analyzing the avian interferon-γ gene according a preferred embodiment of the present invention.

Accordingly, the present invention provides a CpG DNA adjuvant in avian vaccines, which includes an immunostimulatory oligodeoxynucleotide (ODN) having a plurality of TCG tandem repeats at a 5' end, a poly-G structure at a 3' end, and at least one unmethylated CpG motif with avian specific flanking sequences at two ends thereof between the 5' end and the 3' end.

Specifically, the CpG DNA adjuvant in avian vaccines consists of an immunostimulatory oligodeoxynucleotide (ODN) having a sequence including the following formula:

5'TrBbPg3' in which Tr denotes a plurality of TCG tandem repeats at a 5' end of the immunostimulatory ODN, Pg denotes a poly-G structure essentially consisted of 4 to 6 guanines at a 3' end of the immunostimulatory ODN, and Bb denotes a backbone sequence between the 5' end and the 3' end of the immunostimulatory CpG motif. The Bb has at least one CpG motif with avian specific flanking sequences at two ends of the CpG motif. The aforementioned "CpG motif" is referred as an unmethylated dinucleotide sequence containing a cytosine followed by guanine and linked by a phosphodiester bond.

It is worth mentioning that the CpG DNA adjuvant in avian vaccines has the TCG tandem repeats at a 5' end to specifically enhance avian innate and adaptive immune responses, the flanking sequences at two ends of the CpG motif to provide species specificity, the CpG motif itself being the avian immunostimulatory sequence, and the poly-G structure essentially consisted of 4 to 6 guanines at a 3' end to facilitate cellular uptake of the CpG DNA adjuvant. The specific DNA structure of the DNA sequence of the present invention possesses the function of DNA adjuvant in avian vaccines and the risk of the present CpG DNA adjuvant to be digested by DNase is effectively reduced due to its particular structures, rather than that the prior PTO-modified DNA adjuvant by using complicatedly chemical processes.

In a preferred embodiment, the immunostimulatory ODN of the CpG DNA adjuvant in avian vaccines may include but be not limited in a first ODN (CTAGTGTCCA TGACGTTATG GGGGGGT, denoted as SEQ ID NO:1), a second ODN (CTAGTTCGTC GAAGTCGTTT TGGGGGGT, denoted as SEQ ID NO:2), a third ODN (CTAGTTCGAT CATCGTTGAG GGGGGT, denoted as SEQ ID NO:3) or any combination thereof. Those immunostimulatory ODNs are listed as Table 1:

TABLE 1

| SEQ ID NO | Sequence |
|---|---|
| 1 | 5'- <u>CTAGTGTCCA</u> T<span style="border:1px solid">G ACGTT</span>ATG GGGGGG<u>T</u> -3'<br>   SpeI          CpG motif      XbaI |
| 2 | 5'- <u>CTAGTTCGTC</u> GAA<span style="border:1px solid">GTCGTT</span>TTGGGGGG<u>T</u> -3'<br>   SpeI          CpG motif      XbaI |
| 3 | 5'- <u>CTAGTTCGAT</u> C<span style="border:1px solid">ATCGTT</span>GAG GGGGG<u>T</u> -3'<br>   SpeI          CpG motif      XbaI |

As shown in Table 1, the first ODN, the second ODN and the third ODN may be useful examples as the immunostimulatory ODN of the CpG DNA adjuvant in avian vaccines. The species-specific CpG motif has exemplary sequences listed as the boxed letters in Table 1, including but not being limited to, for example, GACGTT, GTCGTT, or ATCGTT from 5' end to 3' end, however, GTCGTT is preferred. Secondly, according to a preferred embodiment of the present invention, the immunostimulatory ODN may optionally include a first restriction enzyme site at the 5' end and a second restriction enzyme site at the 3' end, and the second restriction enzyme site is different from the first restriction enzyme site in sequence. However, it is necessarily mentioned that, the first restriction enzyme site at the 5' end and the second restriction enzyme site at the 3' end of the immunostimulatory ODN of the present invention are designed to ligate into a vector to form a recombinant plasmid, so as to transform a competent cell (for example, E. coli) with the recombinant plasmid for large-scale production. Hence, the sequences of the first restriction enzyme site and the second restriction enzyme site are dependent on the desired vector rather than limiting to the aforementioned sequences. In addition, the sequences of the first restriction enzyme site and the second restriction enzyme site can also be applied to another recombinant recombinant plasmid for producing multiple CpG motifs. In a preferred embodiment, the first restriction enzyme site at the 5' end of the immunostimulatory ODN may be, for example, SpeI site as the single-underlined sequence of CTAGT (i.e. SpeI recognizes and cuts the 6 bp sequence of 5'-ACTAGT-3' to leave five overhanging residues CTAGT); besides, the second restriction enzyme site at the 3' end of the immunostimulatory ODN may be, for example, XbaI site as the double-underlined sequence of T (i.e. XbaI recognizes and cuts the 6 hp sequence of 5'-TCTAGA-3' to leave one overhanging residue T).

Additionally, the CpG DNA adjuvant in avian vaccines can be ligated into vectors to form recombinant plasmids, followed by transforming the competent cells (for example, *E. coli*) for large-scale production. Since the DNA ligation with the vector, transformation, large-scale production are subjected to the conventional methods understood by a person skilled in the art, the related details are unnecessary to be addressed herein.

It is understood that the CpG DNA adjuvant in avian vaccines produced in large scale and subjected to purification can indeed enhance the expression of interferon-γ (IFN-γ) gene, demonstrated by in vitro co-culture with avian peripheral blood mononucleocytes and splenocytes, as well as in vivo immune tests on experimental animals.

Thereinafter, various applications of the CpG DNA adjuvant in avian vaccines will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

EXAMPLE 1

Construction of Recombinant Plasmids Containing the CpG DNA Adjuvant in Avian Vaccines, Transformation and Large-Scale Production Thereof EXAMPLE 1 is related to construct recombinant plasmids containing the immunostimulatory ODNs of the CpG DNA adjuvant in avian vaccines, transformation and large-scale production thereof, in which the immunostimulatory ODNs are designed to be the first ODN shown as SEQ ID NO:1 (referred as ODN-D1), the second ODN shown as SEQ ID NO:2 (referred as ODN-D2), or the third ODN shown as SEQ ID NO:3 (referred as ODN-D3).

Further, three comparative ODNs designed to be the fourth ODN lack of CpG motif and shown as SEQ ID NO:4 (referred as ODN-C), the fifth ODN containing the CpG motif and shown as SEQ ID NO:5 (referred as ODN-S1), or the sixth ODN containing the CpG motif and shown as SEQ ID NO:6 (referred as ODN-S2) are also utilized in EXAMPLE 1. With respect to the fifth ODN, see Wang X. et al., *Avian Disease* 47(9):5-12 (February 2003), the title as "Efficacy of DNA vaccines against infectious bursal disease virus in chickens enhanced by coadministration with CpG oligodeoxynucleotide". With respect to the sixth ODN, see Gomis S. et al., *Infection and Immunity* 71(2):857-863 (February 2003), the title as "Protection of Chickens against *Escherichia coli* Infections by DNA Containing CpG Motifs". Those immunostimulatory ODNs are listed as Table 2:

TABLE 2

| SEQ ID NO | Sequence |
|---|---|
| 4 | 5'- <u>CTAGT</u>CCATG GCCATGGCCA TGG<u>T</u> -3'<br>SpeI                                                             XbaI |
| 5 | 5'- <u>CTAGT</u>GTCCA T<span style="border:1px solid">GACGTT</span>CCT GACGTT<u>T</u> -3'<br>SpeI                CpG motif        XbaI |
| 6 | 5'- <u>CTAGT</u>TCGTC GTT<span style="border:1px solid">GTCGTT</span>T TGTCGTT<u>T</u> -3'<br>SpeI                CpG motif        XbaI |

Next, the first to sixth ODNs are optionally constructed into commercial vectors for large-scale production of the recombinant plasmids containing the first to sixth ODNs. In a preferred embodiment of the present invention, the DNA fragments of the first to sixth ODNs amplified by primers can be subjected to following evaluation of the avian immunostimulating activity in vitro and/or in vivo.

However, in another embodiment, the amplified DNA fragments are further constructed into the commercial vectors, for example, pGEM®T-Easy vector (Promega Corp., Madison, Wis., USA), respectively, to form recombinant plasmids. And then, suitable host cells, for example, competent cells of *E. coli* strain DH5α, are transformed with the recombinant plasmids. In this embodiment, at least one set of the amplified DNA fragments having CpG motif can be constructed into the commercial vectors, for example, pGEM®T-Easy vector (Promega Corp., Madison, Wis., USA), in which the amplified DNA fragments in each recombinant plasmid may be 1 or up to 20 sets arranged in a sequence or with spacer there between. The amplified DNA fragments having CpG motif can be also more than 20 sets constructed in each recombinant plasmid, rather than being limited to the aforementioned quantity, even up to 32 or more sets therein.

After antibiotic selection and sequencing confirmation, the selected clone can be subjected to large-scale production. That is to say, the immunostimulatory ODNs utilized as CpG DNA adjuvant in avian vaccines can be produced in large scale by using bacteria. The construction of recombinant plasmids, transformation of the bacteria, large-scale production, purification of plasmid DNA, measurement of optical density (OD) of DNA at 260 nm, establishment of the standard curve and the like are known by a person skilled in the art, the related details are unnecessary to be addressed herein.

EXAMPLE 2

Construction of Recombinant Plasmids Containing Avian β-Actin Gene and Interferon-γ Gene, Transformation and Large-Scale Production Thereof EXAMPLE 2 is related to construction of recombinant plasmids containing avian β-actin gene and interferon-γ gene, respectively, transformation and large-scale production thereof, in which the avian β-actin gene and interferon-γ gene are obtained from chicken peripheral blood mononuclear cells (PBMC) and splenocytes, by using the method disclosed by Haiqi H. et al., *Developmental and Comparative Immunology* 27(6-7):621-627 (2003) titled as "Identification of CpG oligodeoxynucleotide motifs that stimulate nitric oxide and cytokine production in avian macrophage and peripheral blood mononuclear cells". RNA isolation, synthesis of complementary DNA (cDNA), PCR reaction and the primers for cloning chicken β-actin gene and interferon-γ gene herein are referred to the research paper published by Haiqi H. et al. The chicken β-actin gene is cloned by a PCR reaction with a first upstream primer shown as SEQ ID NO:7 and a first downstream primer shown as SEQ ID NO:8, and the chicken interferon-γ gene is cloned by a second upstream primer shown as SEQ ID NO:9 and a second downstream primer shown as SEQ ID NO:10. The first upstream primer and the first downstream primer referred to the sequence of GenBank Accession No. NM_205518, and the second upstream primer and the second downstream primer referred to the sequence of GenBank Accession No. X99774, are listed below as Table 3:

TABLE 3

| SEQ ID NO | Sequence |
|---|---|
| 7 | 5'-GATTTCGAGCAGGAGATGGCCACAG-3' |
| 8 | 5'-GATCCACATCTGCTGGAAGGTGGAC-3' |
| 9 | 5'-GACATCTCCCAGAAGCTATCTGAGC-3' |
| 10 | 5'-GAGCACAGGAGGTCATAAGATGC-3' |

While performing the PCR reaction, the reaction solution is prepared by using the commercial product, for example, of Invitrogen Corp., Carlsbad, Calif., without being recited in detail herein. Next, the first upstream and downstream primer pair, and the second upstream and downstream primer pair, are added into the PCR reaction solution respectively to carry out the PCR reaction, in which the reaction condition may be exemplified as the following conditions but not limited thereto. For example, the PCR reaction mixture is firstly heated on 94° C. for 5 minutes for denaturing double-stranded DNA (dsDNA) template to single-stranded DNA (ssDNA) templates. Next, the PCR reaction mixture is repeated for 30 cycles, and each cycle comprises a denaturation step on 94° C. for 1 minute, an annealing step for annealing the primer pair to the ssDNA template on 60-70° C. for 30 seconds to 1 minute, and an extension step on 68° C. for 1 minute. Preferably, the annealing step is performed on 65° C. for 45 seconds. After repeating the 30 cycles, the PCR reaction mixture is ended with the prolonged last extension step on 68° C. for 5 minutes for ensuring the PCR reaction more completely.

Besides, the second upstream and downstream primer pair is added into the PCR reaction solution to carry out the PCR reaction, in which the reaction condition may be exemplified as the following conditions but not limited thereto. For example, the PCR reaction mixture is firstly heated on 94° C. for 5 minutes for denaturing dsDNA template to ssDNA templates. Next, the PCR reaction mixture is repeated for 30 cycles, and each cycle comprises a denaturation step on 94° C. for 30 seconds, an annealing step for annealing the primer pair to the ssDNA template on 60-70° C. for 30 seconds to 1 minute, and an extension step on 68° C. for 1 minute. Preferably, the annealing step is performed on 65° C. for 45 seconds. After repeating the 30 cycles, the PCR reaction mixture is ended with the prolonged last extension step on 68° C. for 5 minutes for ensuring the PCR reaction more completely.

After the aforementioned PCR reactions, a DNA fragment of β-actin gene amplified by the first upstream and downstream primer pair has a full length of 408 base pairs (bp) approximately, another DNA fragment of interferon-γ gene amplified by the second upstream and downstream primer pair has a full length of 571 bp approximately. The two DNA fragments are purified and further constructed into pGEM®T-Easy vector (Promega Corp., Madison, Wis., USA) with the same as EXAMPLE 1, respectively, to form recombinant plasmids. And then, suitable host cells, for example, competent cells of E. coli strain DH5α, are transformed with the recombinant plasmids. After antibiotic selection and sequencing confirmation, the restriction enzyme E.coRI digestion and the analysis by DNA electrophoresis are employed to check that the target gene fragments are inserted in the recombinant plasmids and their sequences are correct. Results of DNA electrophoresis of PCR reactions are shown as FIGS. 1A and 1B.

Reference is made to FIGS. 1A and 1B, in which FIG. 1A is an electrophoresis image of PCR reaction product for analyzing the avian β-actin gene according a preferred embodiment of the present invention, FIG. 1B is an electrophoresis image of PCR reaction product for analyzing the avian interferon-γ gene according a preferred embodiment of the present invention, and FIGS. 1A and 1B are employed to determine that the DNA fragment inserted in the recombinant plasmids can be amplified in the correct size. In FIGS. 1A and 1B, the lane M is referred as DNA marker of 100 bp DNA ladder, and the "500 bp" labeled on the left of the lane M is referred as a site of the DNA ladder with 500 bp. In FIG. 1A, the lane 1 is referred as the inserted DNA fragment of the avian β-actin gene with 408 bp approximately as indicated by Arrow 101. In FIG. 1B, the lane 1 is referred as the inserted DNA fragment of the avian interferon-γ gene with 571 bp approximately as indicated by Arrow 103.

According to the results of FIGS. 1A and 1B, the recombinant plasmids containing avian β-actin gene and interferon-γ gene constructed by the present invention can be amplified to the target DNA fragments in the correct size.

EXAMPLE 3

Evaluation of In Vitro Immunostimulatory Activity on Chicken Cells Using CpG DNA Adjuvant in Avian Vaccines EXAMPLE 3 is related to observe interferon-γ gene expression on the primary cultures of chicken PBMCs and splenocytes using the immunostimulatory ODNs of the first to third ODNS (i.e. ODN-D1, ODN-D21 and ODN-D3) in EXAMPLE 1, so as to evaluation of in vitro immunostimulatory activity on chicken cells using CpG DNA adjuvant in avian vaccines.

1. Purification and Culture of Chicken PBMCs

In this embodiment, peripheral blood of 21-day old White Leghorn chickens is collected by cardiac puncture and diluted with 4-fold volume of Hank's balanced salt solution (HBSS) containing the anticoagulant Heparin, in which HBSS and Heparin is mixed with equal volume. The anticoagulated blood is centrifuged to remove plasma at 1350×g for 10 minutes, and the remaining "buffy coat", which is the fraction of the anticoagulated blood sample after centrifugation that contains most of the leukocytes and platelets, is diluted and mixed well with 2-fold volume of HBSS. Next, 3-ml of FICOLL-HYPAQUE® solution (Sigma-Aldrich Co., MO, USA) for lymphocyte separation is added in a tube, followed by carefully laying the diluted buffy coat over the FICOLL-HYPAQUE® solution. While a clear interface is present, the buffy coat is formed by centrifugation at 2250×g for 10 minutes in a horizontal centrifuge, so as to obtain PBMC pellet. The PBMC pellet is resuspended in HBSS and centrifuged at 900×g for 10 minutes, and the two steps are repeated three times. Subsequently, the PBMC is resuspended in RPMI1640 complete medium (Sigma-Aldrich Co., MO, USA) with cell density of $1 \times 10^7$ cells/mL approximately, and 0.5 mL of the PBMC is cultured in each well of a 24-well cell culture plate.

2. Purification and Culture of Chicken Splenocytes

In this embodiment, chicken spleens are aseptically obtained from 21-day old White Leghorn chickens and washed by HBSS. The drawn spleens are mildly homogenized on a grid with 100 μm mesh, for obtaining splenic single-cell suspension. The splenic single-cell suspension is washed by HBSS and centrifuged at 900×g for 10 minutes, and the two steps are repeated three times. Subsequently, the splenocytes are resuspended in RPMI1640 complete medium (Sigma-Aldrich Co., MO, USA) with cell density of $1 \times 10^7$ cells/mL approximately, and 0.5 mL of the PBMC is cultured in each well of a 24-well cell culture plate.

Figure 2:
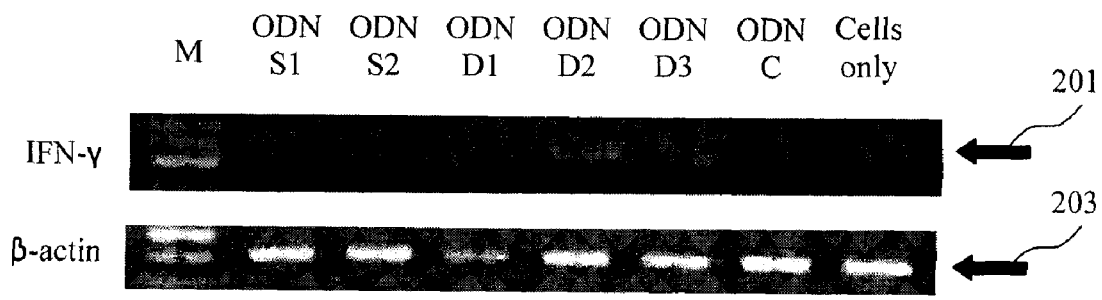
FIG. 2 is an electrophoresis image of semi-quantitative RT-PCR product for analyzing the chicken interferon-γ gene and β-actin gene expression of the PBMC cells according a preferred embodiment of the present invention.
Figure 3:
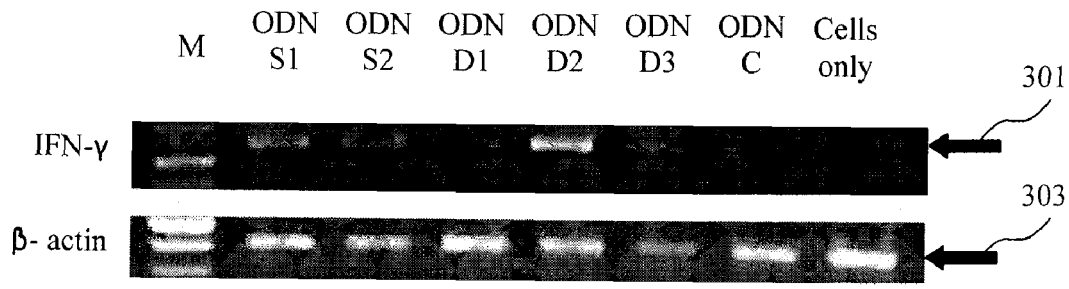
FIG. 3 is an electrophoresis image of semi-quantitative RT-PCR product for analyzing the chicken interferon-γ gene and β-actin gene expression of the splenocytes according a preferred embodiment of the present invention.

3. Evaluation of In Vitro Immunostimulatory Activity on Chicken Lymphocytes Using CpG ODN In this embodiment, 5 μM of the first ODN shown as SEQ ID NO:1 (referred as ODN-D1), the second ODN shown as SEQ ID NO:2 (referred as ODN-D2), and the third ODN shown as SEQ ID NO:3 (referred as ODN-D3) disclosed in EXAMPLE 1 are respectively added into the chicken PBMC and splenocytes that are separated and cultured by this EXAMPLE, and followed by incubating in the incubator at 37° C. in 5% $CO_2$ for 6 hours. The chicken PBMC culture is centrifuged at 900×g for 10 minutes, in which the supernatant is stored at −70° C. approximately, and the PBMC cell pellet is subjected to total RNA extraction by using Trizol® reagent (Invitrogen Corp., Carlsbad, Calif.). The total RNA of the PBMC cells is subjected to semi-quantitative reverse transcription-PCR (Semi-Quantitative RT-PCR), so as to determine the interferon-γ gene expression of the PBMC cells, and to determine the β-actin gene expression thereof as a housekeeping gene, thereby evaluating in vitro immunostimulatory activity on chicken lymphocytes using the CpG DNA adjuvant in avian vaccines of EXAMPLE 1. Herein, the "housekeeping gene" is referred to a gene constitutively expressed and involved in basic functions needed for the sustenance of the cell, and thus the housekeeping gene is subjected to semi-quantitative RT-PCR as an internal standard. FIG. 2 is an electrophoresis image of semi-quantitative RT-PCR reaction product for analyzing the chicken interferon-γ gene and β-actin gene expression of the PBMC cells according a preferred embodiment of the present invention, in which the chicken interferon-γ gene and β-actin gene expression are calculated as integrated optical density (I. O. D.) and shown in Table 4. FIG. 3 is an electrophoresis image of semi-quantitative RT-PCR reaction product for analyzing the chicken interferon-γ gene and β-actin gene expression of the splenocytes according a preferred embodiment of the present invention, in which the chicken interferon-γ gene and β-actin gene expression are calculated as I. O. D. and shown in Table 5.

In FIGS. 2 and 3, the lane M is referred as DNA marker of 100 bp DNA ladder, the amplified DNA fragment of the chicken interferon-γ gene with 571 bp approximately as indicated by Arrows 201 and 301, and the amplified DNA fragment of the chicken β-actin gene with 408 bp approximately as indicated by Arrows 203 and 303. The "ODN-S1" is referred to the gene expression result supplied with the fifth ODN (ODN-S1). The "ODN-S2" is referred to the gene expression result supplied with the sixth ODN (ODN-S2). The "ODN-D2" is referred to the gene expression result supplied with the second ODN (ODN-D2). The "ODN-D3" is referred to the gene expression result supplied with the third ODN (ODN-D3). The "ODN-C" is referred to the gene expression result supplied with the fourth ODN (ODN-C). The "cell only" is referred to the gene expression result without any ODN. The I. O. D. value of Tables 4 and 5 is analyzed and calculated by the image acquisition and analysis software (LabWorks, UVP l.l.c., CA, USA).

TABLE 4

| Gene expression (I.O.D) | CpG DNA adjuvant in avian vaccines | | | | | | |
|---|---|---|---|---|---|---|---|
| | ODN-S1 | ODN-S2 | ODN-D1 | ODN-D2 | ODN-D3 | ODN-C | Cell only |
| IFN-γ | 5.1 | 1.6 | 7.1 | 41.4 | 14.5 | 0.8 | 8.0 |
| β-actin | 100.8 | 101.6 | 47.4 | 101.8 | 86.4 | 115.5 | 110.3 |
| Ratio (IFN-γ/β-actin) | 0.05 | 0.02 | 0.15 | 0.41 | 0.17 | 0.01 | 0.01 |

TABLE 5

| Gene expression (I.O.D) | CpG DNA adjuvant in avian vaccines | | | | | | |
|---|---|---|---|---|---|---|---|
| | ODN-S1 | ODN-S2 | ODN-D1 | ODN-D2 | ODN-D3 | ODN-C | none |
| IFN-γ | 91.8 | 50.8 | 13.3 | 160.0 | 34.8 | 16.5 | 4.9 |
| β-actin | 76.9 | 55.8 | 79.8 | 61.4 | 31.6 | 70.0 | 101.5 |
| Ratio (IFN-γ/β-actin) | 1.19 | 0.91 | 0.17 | 2.60 | 1.10 | 0.23 | 0.05 |

In view of the results from FIGS. 2, 3, Tables 4 and 5, the CpG DNA adjuvant in avian vaccines of the present invention effectively enhances the interferon-γ gene expression of the chicken PMBC and splenocytes, and the second ODN (ODN-D2) has better enhancement of the interferon-γ gene expression of the chicken PMBC and splenocytes. Since the CpG DNA adjuvant in avian vaccines of the present invention has beneficially immunostimulatory activity to the chicken PMBC and splenocytes, and the interferon-γ gene expression of the chicken PMBC and splenocytes is related to avian innate immunity. That is to say, the CpG DNA adjuvant in avian vaccines of the present invention specifically enhances the avian specifically enhance avian innate and adaptive immune responses.

EXAMPLE 4

Figure 4:
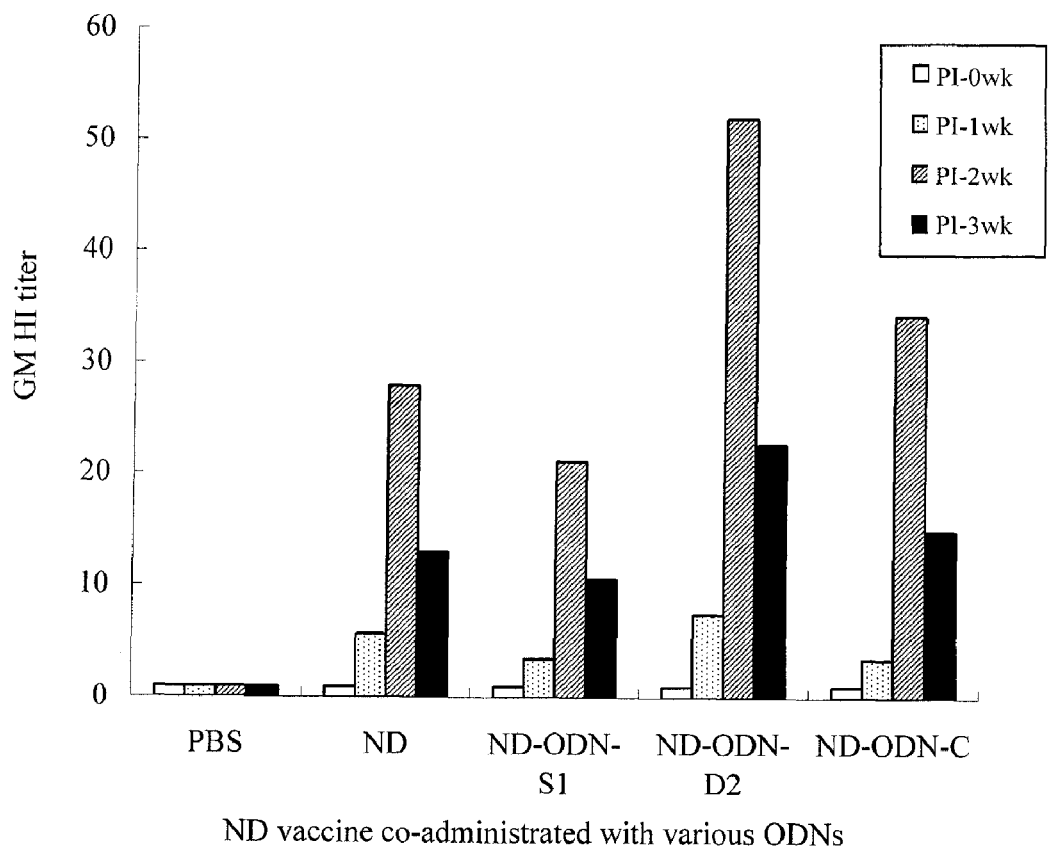
FIG. 4 is a bar chart of HI titer of chickens co-immunized with the ND commercialized vaccine and the CpG DNA adjuvant according to a preferred embodiment of the present invention.
Figure 6:
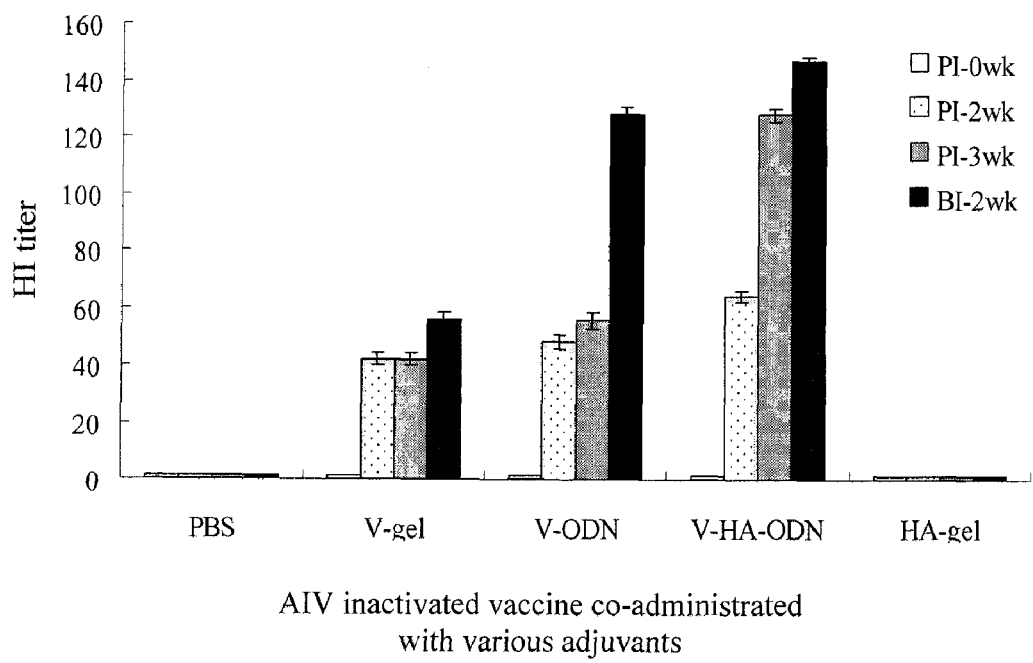
FIG. 6 is a bar chart of HI titer of chickens co-immunized with various AIV inactivated vaccine mixtures containing the CpG DNA adjuvant and/or H5 subunit protein according to a preferred embodiment of the present invention.
Figure 7:
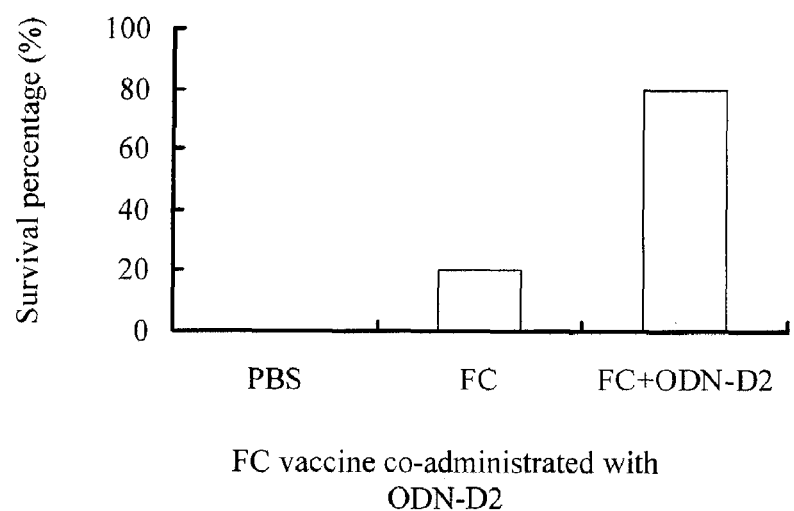
FIG. 7 is a bar chart of survival percentage of the ICR mice co-immunized with the fowl cholera inactivated bacterin and the CpG DNA adjuvant according to a preferred embodiment of the present invention.

Evaluation of In Vivo Immunostimulatory Activity on Chickens Using CpG DNA Adjuvant in Avian Vaccines 1. Evaluation of In Vivo Immunostimulatory Activity on Chickens Using Newcastle Disease Vaccine Supplied with CpG DNA Adjuvant In this EXAMPLE, the one-day-old specific pathogen free (SPF) chickens are subjected to intra-muscular immunization by using Newcastle Disease (ND) vaccine, for example, ND live vaccine, at a dose of 0.5 mL per chicken, supplied with the fifth ODN shown as SEQ ID NO:5 (referred as ODN-S1), the second ODN shown as SEQ ID NO:2 (referred as ODN-D2), and the fourth ODN shown as SEQ ID NO:4 (referred as ODN-C) disclosed in EXAMPLE 1 at a dose of 50 μg in 0.5 mL, respectively. After immunization, one week, two weeks, or three weeks post-immunization, the chicken blood is collected to analyze hemagglutination inhibition titer (HI titer) against ND virus, thereby evaluating in vivo immunostimulatory activity on chickens using ND vaccine supplied with various ODNs (CpG DNA adjuvants). The aforementioned result is shown in FIG. 4. In addition, after the first blood drawing, the chickens of which have been drawn their blood after three weeks post-immunization are booster immunized by the same vaccine with the prime immunization, followed by being sacrificed to obtain their splenocytes. In order to analyze the avian innate and adaptive immune responses, the splenocytes are subjected to BrdU (Bromodeoxyuridine, analogue of thymidine) assay (Diagnostics Corporation, Indianapolis, Ind., USA) to measure cell proliferation, and the stimulation index (SI) is calculated as that the BrdU chemiluminescence intensity incorporated into cells with Concanavalin A (Con A, a kind of plant hemagglutinin) stimulation is divided by the one without Con A stimulation. The percentage of CD4□/CD8□ cells is measured by anti-CD4 monoclonal antibody (CT-4; Beckman-Coulter, Miami, Fla., USA) and anti-CD8 monoclonal antibody (CT-8; Beckman-Coulter). The above results are shown in FIGS. 5A to 5C.

Reference is made to FIG. 4, which is a bar chart of HI titer of chickens co-immunized with the ND commercialized vaccine and the CpG DNA adjuvant according to a preferred embodiment of the present invention. In FIG. 4, the horizontal axis is referred as ND commercialized vaccine supplied with various ODNs, in which "PBS" is referred as immunization with ND commercialized vaccine and phosphate buffer solution (PBS), "ND" is referred as mere immunization with ND commercialized vaccine, "ND-ODN-S1" is referred as co-immunization with ND commercialized vaccine and the fifth ODN (ODN-S1), "ND-ODN-D2" is referred as co-immunization with ND commercialized vaccine and the second ODN (ODN-D2), "ND-ODN-C" is referred as co-immunization with ND commercialized vaccine and the fourth ODN (ODN-C, without CpG motif); the vertical axis is referred as geometric mean (GM) HI titer; a blank bar is referred as GM HI titer of the chicken blood collected post immunization (PI-0 wk), a spotted bar is referred as GM HI titer of the chicken blood collected on one week post-immunization (PI-1 wk), a striped bar is referred as GM HI titer of the chicken blood collected on two weeks post-immunization (PI-2 wk), a black bar is referred as GM HI titer of the chicken blood collected on three weeks post-immunization (PI-3 wk).

In view of the results from FIG. 4, according to the chicken blood collected on two weeks post-immunization (PI-2 wk), the chickens co-immunized with the second ODN of the CpG DNA adjuvant in avian vaccines of the present invention and ND commercialized vaccine has higher GM HI titer than the one calculated from the immunization of the ND commercialized vaccine. In other word, the ND commercialized vaccine supplied with the second ODN significantly enhances the immunostimulatory activity of the ND commercialized vaccine. Moreover, the co-immunization with the second ODN of the CpG DNA adjuvant in avian vaccines of the present invention and ND commercialized vaccine can provide chickens with longer immune protection even prolonging to almost three weeks, and the immune protection ability is significantly better than the immunization with ND commercialized vaccine or the co-immunization with ND commercialized vaccine and other ODNs.

Reference is made to FIGS. 5A to 5C, which are bar charts of stimulation index (SI) (FIG. 5A), CD8□ cell percentage (FIG. 5B), and CD4□ cell percentage (FIG. 5C) of chickens co-immunized with the ND vaccine and various CpG DNA adjuvant according to a preferred embodiment of the present invention, respectively. The horizontal axis of FIGS. 5A to 5C is referred as ND commercialized vaccine supplied with various ODNs (CpG DNA adjuvants), in which "Control" or "PBS" is referred as immunization with PBS but no ND commercialized vaccine, "NDL" is referred as mere immunization with ND commercialized vaccine, "NDL-ODN-S1" is referred as co-immunization with ND commercialized vaccine (for example, ND live vaccine) and the fifth ODN (ODN-S1), "NDL-ODN-D2" is referred as co-immunization with ND commercialized vaccine (for example, ND live vaccine) and the second ODN (ODN-D2), "NDL-ODN-C" is referred as co-immunization with ND commercialized vaccine (for example, ND live vaccine) and the fourth ODN (ODN-C, without CpG motif). The vertical axis of FIG. 5A is referred as stimulation index (SI) of chicken splenocytes, the vertical axis of FIG. 5B is referred as CD8□ cell percentage, and the vertical axis of FIG. 5C is referred as CD4□ cell percentage.

In view of the results from FIGS. 5A to 5C, according to the chicken splenocytes, CD4□ and CD8□ cells collected on two weeks post-immunization (PI-2 wk), the chickens co-immunized with the second ODN of the CpG DNA adjuvant in avian vaccines of the present invention and ND commercialized vaccine has significantly higher SI of splenocytes, higher CD□ and CD□ cell percentage than the ones calculated from the immunization of the ND commercialized vaccine or the co-immunization with ND commercialized vaccine and other ODNs.

2. Evaluation of In Vivo Immunostimulatory Activity on Chickens Using Avian Influenza Virus Vaccine Supplied with CpG DNA Adjuvant The avian influenza virus (AIV) inactivated vaccine utilized in this EXAMPLE is supplied with the second ODN (ODN-D2) disclosed in EXAMPLE 1 as the CpG DNA adjuvant. In this EXAMPLE, the 3-week old White Leghorn chickens are divided into five groups, and each group has 5 chickens immunized with PBS, or various vaccine mixtures that may contain at least one of inactivated avian influenza virus (denoted as V), avian influenza viral H5 subunit protein expressed in Prokaryotic system (denoted as HA at a dose of 15 μg per chicken), the second ODN (ODN-D2, at a dose of 30 μg per chicken), conventional adjuvant such as aluminum hydroxide gel (Al-gel), or any combinations thereof. Those chickens are subjected to intra-muscular immunization by using PBS or the above vaccine mixtures at a dose of 1 mL per chicken, followed by collecting the chicken blood after immunization (PI-0 wk), or on one week (PI-1 wk), two weeks (PI-2 wk), or three weeks (PI-3 wk) post immunization. Besides, the chickens of which have been immunized on three weeks post-immunization (PI-3 wk) are booster immunized by the same vaccine with the prime immunization, followed by blood collecting on two weeks after booster immunization (BI-2 wk). The collected blood is subjected to analyze HI titer against inactivated avian influenza virus, thereby evaluating in vivo immunostimulatory activity on chickens using avian influenza inactivated vaccine supplied with the CpG DNA adjuvant. The result is shown in FIG. 6.

Reference is made to FIG. 6, which is a bar chart of HI titer of chickens co-immunized with various AIV inactivated vaccine mixtures containing the CpG DNA adjuvant and/or H5 subunit protein according to a preferred embodiment of the present invention. The horizontal axis of FIG. 6 is referred as the AIV inactivated vaccine supplied with various adjuvants, in which "PBS" is referred as immunization with PBS but no AIV inactivated vaccine as a control; "V-gel" is referred as co-immunization with the AIV inactivated vaccine containing AIV inactivated virus and conventional Al-gel adjuvant; "V-ODN" is referred as co-immunization with the AIV inactivated vaccine and the second ODN (ODN-D2); "V-HA-ODN" is referred as co-immunization with the AIV inactivated vaccine, H5 subunit protein (HA) and the second ODN (ODN-D2); "HA-gel" is referred as co-immunization with H5 subunit protein (HA) and conventional Al-gel adjuvant. The vertical axis of FIG. 6 is referred as HI titer of the chicken blood; a blank bar is referred as HI titer of the chicken blood collected post immunization (PI-0 wk), a spotted bar is referred as HI titer of the chicken blood collected on two weeks post-immunization (PI-2 wk), a gray bar is referred as HI titer of the chicken blood collected on three weeks post-immunization (PI-3 wk), a black bar is referred as HI titer of the chicken blood collected on two weeks after booster immunization (BI-2 wk).

In view of the results from FIG. 6, the HI titer of the chicken blood collected from the chickens immunized with AIV inactivated vaccine and the second ODN (ODN-D2), on two or three weeks post-immunization, or two weeks after booster immunization (BI-2 wk), is significantly higher than the one collected from the chickens immunized with AIV inactivated vaccine and various adjuvants, or PBS. In other word, supplying with the second ODN can significantly enhance the immunostimulatory activity of the AIV inactivated vaccine.

3. Evaluation of In Vivo Immunostimulatory Activity on Chickens Using Fowl Cholera Inactivated Bacterin Supplied with CpG DNA Adjuvant The fowl cholera inactivated bacterin (made in Taiwan) utilized in this EXAMPLE is supplied with the second ODN (ODN-D2) disclosed in EXAMPLE 1 as the CpG DNA adjuvant. In this EXAMPLE, the ICR mice are divided into groups, and each group has 10 mice with averaged weight of 14 g. The ICR mice are subjected to subcutaneous immunization with fowl cholera inactivated bacterin (denoted as FC, at a dose of 0.2 mL per mouse), or fowl cholera inactivated bacterin supplied with the second ODN (ODN-D2, at a dose of 5 μg per mouse). Two weeks post-immunization, each mouse is challenged with fowl cholera live bacteria (*Pasturella multocida*) at 10-fold minimal lethal dose (10 MLD) of 0.1 mL by using subcutaneous injection, followed by calculating the quantity of survivals. The result is shown in FIG. 7.

Reference is made to FIG. 7, which is a bar chart of survival percentage of the ICR mice co-immunized with the fowl cholera inactivated bacterin and the CpG DNA adjuvant according to a preferred embodiment of the present invention. The horizontal axis of FIG. 7 is referred as the fowl cholera inactivated bacterin supplied with various adjuvants, in which "PBS" is referred as immunization with PBS but no fowl cholera inactivated bacterin as a control; "FC" is referred as mere immunization with the fowl cholera inactivated bacterin; and "FC □ ODN-D2" is referred as co-immunization with the fowl cholera inactivated bacterin and the second ODN (ODN-D2). The vertical axis of FIG. 7 is referred as survival percentage (%).

In view of the results from FIG. 7, the survival percentage of the ICR mice co-immunized with the fowl cholera inactivated bacterin and the second ODN (ODN-D2) (80% of survival percentage approximately) is significantly higher than the one of the mice immunized with the fowl cholera inactivated bacterin (20% of survival percentage approximately) or PBS (0% of survival percentage approximately). In other word, supplying with the second ODN can significantly enhance the immunostimulatory activity of the fowl cholera inactivated commercialized bacterin.

In addition, it is necessarily mentioning that, specific immunostimulatory ODNs, specific birds (such as chickens) or mice, specific cell types are employed as exemplary embodiments in the present invention for evaluating the immunostimulatory activity of the CpG DNA adjuvants in avian vaccines of the present invention, however, the different CpG DNA adjuvants in avian vaccines of the present invention can be any combined thereof, and the CpG DNA adjuvants in avian vaccines of the present invention also can be applied to other kinds of birds or cell types rather than limiting to the aforementioned examples. Furthermore, as is understood by a person skilled in the art, in addition to ND live vaccine, AIV inactivated vaccine and/or H5 subunit protein, or fowl cholera inactivated bacterin disclosed by the present invention, the CpG DNA adjuvants in avian vaccines of the present invention can be the adjuvant supplied into other avian vaccines, for example, ND attenuated vaccine, ND inactivated vaccine or the like, rather than limiting to the aforementioned vaccines.

According to the preferred embodiments of the present invention, the aforementioned CpG DNA adjuvant in avian vaccines of the present invention, it advantageously includes an immunostimulatory oligodeoxynucleotide (ODN) having a plurality of TCG tandem repeats at a 5' end, a poly-G structure at a 3' end, and at least one CpG motif with avian specific flanking sequences at two ends thereof between the 5' end and the 3' end. The CpG DNA adjuvant in avian vaccines is beneficial to carry out large-scale production, specifically to enhance avian innate and adaptive immune responses, and hardly to be digested by DNase due to its stable structures, instead of the prior DNA adjuvant modified by chemical processes complicatedly.

As is understood by a person skilled in the art, the foregoing preferred embodiments of the present invention are illustrated of the present invention rather than limiting of the present invention. It is intended to cover various modifications and similar arrangements included within the spirit and scope of the appended claims. Therefore, the scope of which should be accorded the broadest interpretation so as to encompass all such modifications and similar structure.

What is claimed is:

1. A CpG DNA adjuvant in avian vaccines, the CpG DNA adjuvant in avian vaccines has an immunostimulatory oligodeoxynucleotide (ODN) having a sequence of SEQ ID NO: 2.

2. The CpG DNA adjuvant in avian vaccines according to claim 1, wherein the avian vaccines are Newcastle Disease (ND) live vaccine, ND inactivated vaccine, avian influenza inactivated vaccine, or fowl cholera inactivated bacterin.

3. The CpG DNA adjuvant in avian vaccines according to claim 2, wherein the avian influenza inactivated vaccine further comprises an avian influenza viral H5 subunit protein.

* * * * *

SEQUENCE LISTING

<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: Chemically synthesized sequence

<400> SEQUENCE: 1
ctagtgtcca tgacgttatg gggggt                                27

<210> SEQ ID NO 2
<211> LENGTH: 28
<212> TYPE: DNA
<213> ORGANISM: Artificial Sequence
<220> FEATURE:
<223> OTHER INFORMATION: Chemically synthesized sequence

<400> SEQUENCE: 2
ctagttcgtc gaagtcgttt tggggggt                              28

<210> SEQ ID NO 3
<211> LENGTH: 26
<212> TYPE: DNA
<213> ORGANISM: Artificial Sequence
<220> FEATURE:
<223> OTHER INFORMATION: Chemically synthesized sequence

<400> SEQUENCE: 3
ctagttcgat catcgttgag ggggt                                 26

<210> SEQ ID NO 4
<211> LENGTH: 24
<212> TYPE: DNA
<213> ORGANISM: Artificial Sequence
<220> FEATURE:
<223> OTHER INFORMATION: Chemically synthesized sequence

<400> SEQUENCE: 4
ctagtccatg gccatggcca tggt                                  24

<210> SEQ ID NO 5
<211> LENGTH: 27
<212> TYPE: DNA
<213> ORGANISM: Artificial Sequence
<220> FEATURE:
<223> OTHER INFORMATION: Chemically synthesized sequence

<400> SEQUENCE: 5
ctagtgtcca tgacgttcct gacgttt                               27

<210> SEQ ID NO 6
<211> LENGTH: 28
<212> TYPE: DNA
<213> ORGANISM: Artificial Sequence
<220> FEATURE:
<223> OTHER INFORMATION: Chemically synthesized sequence

<400> SEQUENCE: 6
ctagttcgtc gttgtcgttt tgtcgttt                              28

<210> SEQ ID NO 7
<211> LENGTH: 25

-continued

```
<212> TYPE: DNA
<213> ORGANISM: Artificial Sequence
<220> FEATURE:
<223> OTHER INFORMATION: Chemically synthesized sequence

<400> SEQUENCE: 7
gatttcgagc aggagatggc cacag                                          25

<210> SEQ ID NO 8
<211> LENGTH: 25
<212> TYPE: DNA
<213> ORGANISM: Artificial Sequence
<220> FEATURE:
<223> OTHER INFORMATION: Chemically synthesized sequence

<400> SEQUENCE: 8
gatccacatc tgctggaagg tggac                                          25

<210> SEQ ID NO 9
<211> LENGTH: 25
<212> TYPE: DNA
<213> ORGANISM: Artificial Sequence
<220> FEATURE:
<223> OTHER INFORMATION: Chemically synthesized sequence

<400> SEQUENCE: 9
gacatctccc agaagctatc tgagc                                          25

<210> SEQ ID NO 10
<211> LENGTH: 23
<212> TYPE: DNA
<213> ORGANISM: Artificial Sequence
<220> FEATURE:
<223> OTHER INFORMATION: Chemically synthesized sequence

<400> SEQUENCE: 10
gagcacagga ggtcataaga tgc                                            23
```